United States Patent [19]
Bödecker et al.

[11] Patent Number: 4,626,786
[45] Date of Patent: Dec. 2, 1986

[54] LIQUID CONDUCTIVITY PROBE

[75] Inventors: Kay Bödecker, Chieming; Walter Goth, Reichenhall; Robert Scheurl, Inzell; Hans-Erwin Strasser, Siegsdorf, all of Fed. Rep. of Germany

[73] Assignee: Henkel Kommanditgesellschaft auf Aktien, Duesseldorf, Fed. Rep. of Germany

[21] Appl. No.: 556,034

[22] Filed: Nov. 29, 1983

[30] Foreign Application Priority Data

Dec. 8, 1982 [DE] Fed. Rep. of Germany ....... 3245426

[51] Int. Cl.$^4$ ............................................ G01N 27/02
[52] U.S. Cl. ..................................... 324/449; 324/446
[58] Field of Search ............... 324/445, 446, 447, 448, 324/449, 450, 444; 340/852; 204/242, 435

[56] References Cited

U.S. PATENT DOCUMENTS

| | | | |
|---|---|---|---|
| 1,670,640 | 5/1928 | Smith | 324/446 |
| 3,774,105 | 11/1973 | Henning | 324/449 |
| 3,940,732 | 2/1976 | Hudson et al. | 340/852 |
| 4,091,324 | 5/1978 | Diamond | 324/449 |
| 4,196,384 | 4/1980 | Willenbrock et al. | 324/446 |
| 4,227,151 | 10/1980 | Ellis et al. | 324/448 |
| 4,362,994 | 12/1982 | Goldsmith | 324/446 |
| 4,500,402 | 2/1985 | Miles | 204/435 |

FOREIGN PATENT DOCUMENTS 3006877 9/1981 Fed. Rep. of Germany ...... 324/449

OTHER PUBLICATIONS

Journal of Physical Chemistry, Sep. 1954, pp. 696–699, "New Cell Design for Precision Conductimetry'-'—James C. Nichol.
McGraw Hill Encyclopedia of Science and Technology, pp. 624–625, "Polyether Resins"—Oct. 27, 1982.

*Primary Examiner*—Reinhard J. Eisenzopf
*Assistant Examiner*—Jack B. Harvey
*Attorney, Agent, or Firm*—Ernest G. Szoke; Nelson Littell, Jr.; Henry E. Millson, Jr.

[57] ABSTRACT

This invention relates to an electrical measuring probe for determining the electrical conductivity of a liquid comprising a measuring zone extending longitudinally through the probe, through which the liquid to be measured flows and to which an electrical current is applied between electrodes, the electrodes having electrical leads remote from the liquid to be measured and those parts of the electrodes remote from the liquid to be measured forming a mechanically stabilizing and electrically conductive insertion or conductor frame of an electrically insulating sleeve which determines the shape of the probe. The insertion frame contains individual conductors in the sleeve distributed axially symmetrically in relation to the longitudinal axis of the probe, and the sleeve is made by injection-molding and consists of a chemically stable thermoplastic.

5 Claims, 5 Drawing Figures

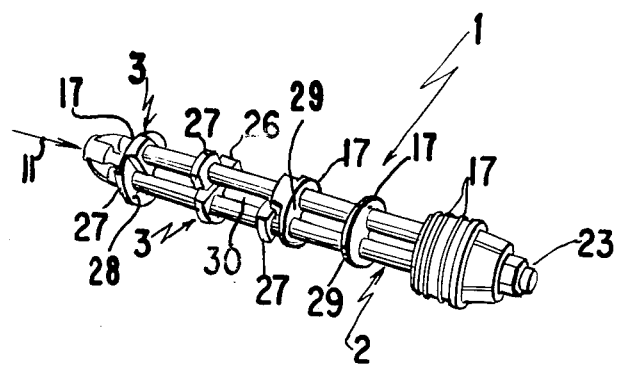

LIQUID CONDUCTIVITY PROBE

FIELD OF THE INVENTION

This invention relates to an electrical measuring probe. More specifically, this invention relates to an electrical measuring probe for determining the electrical conductivity of a liquid and to a method of making same.

BACKGROUND OF THE INVENTION

Electrical measuring probes that measure the electrical conductivity of liquids are used, for example, to check the concentration of cleaning and disinfecting solutions in pressurized pipelines. In cases such as these, the electrical resistance of the product to be measured, i.e., the liquid, is generally measured. Where the liquid to be measured is of a chemically aggressive nature, those parts of the measuring probe which come into contact with it have to be sufficiently chemically resistant. The measuring probe also has to be designed in such a way that its accuracy of measurement does not suffer under the effect of variations in temperatures, for example, between 10° and 95° C.

The measuring probes are mostly made of machined, semi-finished thermoplastics, the electrical connection with the liquid to be measured being established by means of shaped elements of electrocarbon, fine steel, or noble metal. The seals between the electrically conductive shaped elements and the plastic parts are established, for example, by means of elastic sealing elements. In one such construction known from U.S. Pat. No. 4,227,151, several circular electrodes arranged concentrically are insulated from one another by intermediate layers of a thermoplastic.

Operational difficulties are encountered with measuring probes or measuring cells of the above kind due to the different coefficients of thermal expansion of the conductive metal and carbon elements on the one hand and the insulating plastic parts on the other hand. This results in cracking of the insulating plastic parts, separation at the interfaces, and deterioration in the bias of elastic sealing elements. The resulting leak at the interface between conductive and insulating parts leads both to insulating faults and hence to measurement errors and also to corrosion and destruction of the individual components, particularly the electrical power lead.

Accordingly, German published patent application (DE-OS) No. 30 06 877 proposes a measuring probe particularly designed to supply analog data, in which those parts of the electrical leads which have to be screened off from the liquid to be measured form a mechanically stabilizing insertion frame of an electrically insulating elastomeric sleeve which enters into a so-called rubber-to-metal bond with the constituent material of the leads and which determines the shape of the probe. Although this measuring probe represents an advance over the existing state of the art, it cannot be used in chemically aggressive or corrosive liquids such as nitric acid or caustic soda because known elastomers are not permanently stable under such working conditions. Another problem of the known probe lies in the considerable thermal stresses which still occur in the event of wide variations in temperature.

OBJECTS OF THE INVENTION

It is an object of the invention to provide an electrical measuring probe for determining the electrical conductivity of liquids.

It is also an object of the invention to provide a method of preparing such an electrical measuring probe.

It is a further object of the invention to provide a measuring probe that can be used in highly chemically aggressive media and that supplies satisfactorily measured data even in the event of frequent temperature variations of up to 80° C. and more.

It is yet a further object of the invention to provide an electrical measuring probe for determining the electrical conductivity of a liquid comprising a measuring zone extending longitudinally through the probe, through which the liquid to be measured flows and to which an electrical current is applied between electrodes, the electrodes having electrical leads remote from the liquid to be measured and those parts of the electrodes remote from the liquid to be measured forming a mechanically stabilizing and electrically conductive insertion or conductor frame of an electrically insulating sleeve which determines the shape of the probe wherein the conductor frame contains individual conductors in the sleeve distributed axially symmetrically in relation to the longitudinal axis of the probe and wherein the sleeve consists of a chemically stable thermoplastic plastic in intimate contact with said conductor frame.

These and other objects of the invention will become more apparent in the discussion below.

BRIEF DESCRIPTION OF THE DRAWINGS

FIGS. 4 and 5 each represent an oblique view of said embodiment.

DETAILED DESCRIPTION OF THE INVENTION

Figure 1:
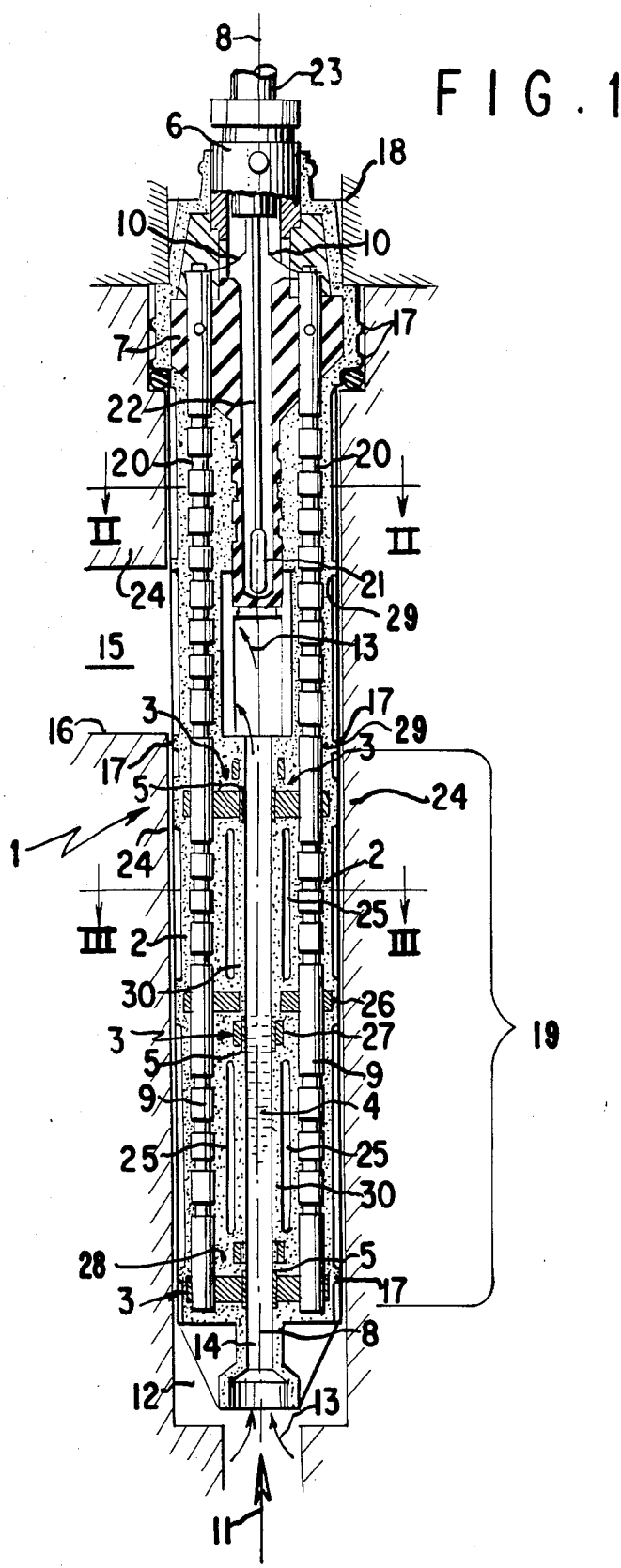
FIG. 1 represents a cross-sectional, longitudinal view of an embodiment of the invention.

According to the invention, an electrical measuring probe comprises a sleeve and an insertion frame in the sleeve containing individual conductors distributed symmetrically in relation to the longitudinal axis of the probe, as the axis of symmetry. The sleeve is made by injection-molding and consists of a chemically stable thermoplastic.

The measuring probe according to the invention, which is preferably designed to supply analog data, comprises a safe connection between insulation and electrical leads and also has the mechanical stability, chemical stability, and resistance to wear required for use in fast-flowing, heavily contaminated media. By virtue of the symmetrical construction, the combined thermal and compressive stresses built up are also symmetrically distributed so that, even under the effect of varying thermal and compressive stresses, there is no separation of the plastic at its interfaces with the metal parts and hence no leaks, nor any measurement errors caused by mechanical-distortion.

According to another aspect of the invention, not only the insertion frame itself but also an insulating receiving element associated therewith, together with an adjoining cable guide, and also the electrodes or measuring elements, particularly of noble metal, which are fixedly connected to the insertion frame and only come into contact with the liquid to be measured, are designed and arranged symmetrically in relation to the axis of symmetry. In this connection, the chemically stable electrically non-conductive thermoplastic is distributed in such a way that it covers the entire frame, including an optional variable resistor plus leads provided for temperature compensation, in such a way that only the measuring surfaces of the measuring elements and the cable guide situated outside the liquid to be measured are exposed.

The measuring probe according to the invention is preferably made by introducing the insertion frame to be covered by the thermoplastic into a mold and injecting thermoplastic into the space not occupied by the frame. The thermoplastic preferably used is an ethylene/tetrafluoroethylene copolymer because such copolymers are of particular value for this very purpose by virtue of their universal chemical stability and their high long-term temperature stability of up to 150° C. The ethylene/tetrafluoroethylene copolymers ETVP 6235 or TFA LP 6500 available from Hoechst AG under the trade mark HOSTAFLON are particularly suitable. A major advantage of this partly crystalline copolymer is its linear to transverse shrinkage ratio of approximately 1:2 upon cooling after the injection process. This favorable shrinkage ratio promotes the establishment of an intimate, pressure-tight bond between the thermoplastic and the metal insertion frame.

To support the combined thermal and compressive stresses occurring in operation, it is particularly favorable according to another aspect of the invention for the metallic conductors of the frame to be sandblasted or notched at certain, preferably regular, intervals. This provides for a so-called form-locking bond between the plastic and the metal insertion frame which virtually prevents these parts from moving relative to one another, even at the interfaces and under intense thermal/-compressive stressing.

Figure 2:
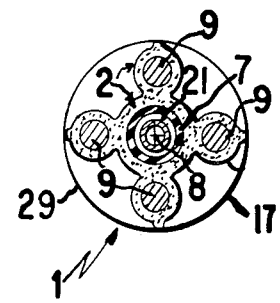
FIGS. 2 and 3 each represent a cross-sectional vertical view of said embodiment.
Figure 3:
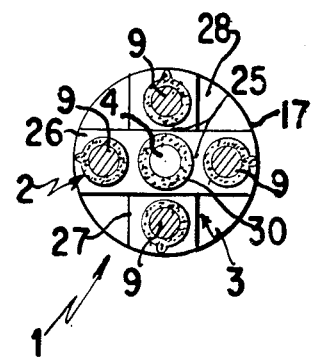

The invention can perhaps be better appreciated by making reference to the drawings. The measuring probe, which is generally denoted by the reference "1" in FIGS. 1 to 5, consists essentially of an injection-molded, electrically insulating thermoplastic sleeve 2 with a stable, metal insertion or conductor frame 3 symmetrically arranged therein. The thermoplastic sleeve 2 houses all those parts of the frame 3 which are not to come into contact with the liquid 4 to be measured. Accordingly, only the electrodes or measuring elements 5, preferably of noble metal, fixedly connected to the frame 3 and the cable guide 6 situated outside the liquid 4 to be measured, remain exposed. In the embodiment illustrated, the metal frame 3, which is held in the similarly encased, insulating receiving element 7, consists essentially of four elongate individual conductors 9 distributed symmetrically around the longitudinal axis 8 of the probe (cf., in particular, FIGS. 2 and 3). By virtue of this axially symmetrical distribution of the individual conductors 9, including their feeder-wires 10, in relation to the cable guide 6, the thermal stresses built up between the plastic sleeve and the metal frame 3 in the event of fluctuations in temperature are unable to cause any distortion of the probe 1.

Regarding the measuring probe shown in FIG. 1, which is designed for use in, for example, throughflow armatures, it is assumed that the liquid 4 to be measured flows from an inlet 11 with a liquid chamber 12 through a longitudinal bore 14 to the liquid chamber 15 at the outlet 16 in the direction of the arrow 13. The liquid is forced to flow along that path by means of sealing edges 17 integrally molded on the thermoplastic sleeve 2 and by a part 18 pressed on at the opposite longitudinal end of the probe 1.

The electrical resistance of the liquid 4 to be measured, flowing from the inlet 11 to the outlet 16 of the throughflow armature, is determined in the measuring zone 19 which is defined by the electrodes or measuring elements 5 and in which a current delivered through the feeder wires 10 and the individual conductors 9 is passed through the liquid 4 to be measured in the measuring zone and the resistance of the liquid is measured. The current should preferably be measured between the middle measuring element of the measuring zone on the one hand and its two end measuring elements on the other hand.

If the individual conductors 9 of the frame 3 which are arranged axially symmetrically in the measuring probe 1 are roughened, for example, sand-blasted, or are provided at more or less regular intervals with notches 20, the mechanical and measuring stability of the probe 1 is considerably improved by comparison with individual conductors 9 having smooth outer surfaces because relative movement is no longer possible, even at the plastic/metal interfaces, by virtue of the form-locking connection established by roughening or notching.

Before assembly and on insertion to join the members of the frame 3 to the body of the thermoplastic sleeve 2, the frame members are best brought into the required spatial relationship by means of the insulating receiving element 7. In addition, the insulating receiving element 7 may contain a variable resistor 21 with leads 22 which is favorable for temperature compensation. The variable resistor leads 22 may be guided outward with the leads 10 of the frame 3 through the cable guide 6 to the connecting cable 23.

Lower part 24 surrounds the probe 1. Upper part 18 and lower part 24, which comprise parts of an instrument for holding probe 1 securely, may snap together. More specifically, upper part 18 may snap onto lower part 24.

The probe 1 has several features that are best appreciated by careful study of the drawings. For example, probe 1 has interstices 25 between the conductors 9, which interestices 25 can be closed during casting. Also, arranged perpendicularly to the conductors 9 are bridges 26 and 27, which originate from a bracing strut 30. Bracing strut 30 contains the longitudinal bore 14 through which the liquid 4 flows. Disc 28 is a thermoplastic circular area which originates from the sealing edge 17. Disc 29 also forms a sealing function.

While the present invention has been illustrated with the aid of certain specific embodiments thereof, it will be readily apparent to others skilled in the art that the invention is not limited to these particular embodiments and that various changes and modifications may be made without departing from the spirit of the invention or the scope of the appended claims.

| COMPONENT LIST | |
|---|---|
| Number | Component |
| 1 | measuring probe |
| 2 | sleeve |
| 3 | conductor frame |
| 4 | liquid |

-continued

COMPONENT LIST

| Number | Component |
|---|---|
| 5 | electrode |
| 6 | cable guide |
| 7 | receiving element |
| 8 | longitudinal axis of probe |
| 9 | individual conductor |
| 10 | feeder wire |
| 11 | inlet |
| 12 | liquid chamber |
| 13 | arrow |
| 14 | longitudinal bore |
| 15 | liquid chamber |
| 16 | outlet |
| 17 | sealing edge |
| 18 | part |
| 19 | measuring zone |
| 20 | notch |
| 21 | variable resistor |
| 22 | leads |
| 23 | connecting cable |
| 24 | lower part of built-in instrument |
| 25 | interstices |
| 26, 27 | plastic-coated bridge |
| 28, 29 | circular area (disc) |
| 30 | bracing strut |

We claim:

1. An electrical measuring probe for determining the electrical conductivity of a liquid comprising a measuring zone extended longitudinally through the probe, through which the liquid to be measured flows, sets of electrodes in contact with said liquid and spaced along said measuring zone to which an electrical current is applied between each set of electrodes, the electrodes having electrode leads remote from the liquid to be measured, said electrode leads being electrically in contact with four individual conductors symmetrically distributed at equal intervals around the longitudinal axis of the probe, said electrode leads electrically in contact with said four individual conductors, said four individual conductors forming a mechanically stabilizing and electrically conductive conductor frame covered with an electrically insulating sleeve, and wherein the sleeve consists of a chemically stable thermoplastic in intimate contact with said conductor frame, said measuring zone leading to a liquid outlet, said conductor frame being connected to an insulating receiving element in turn connected to an adjoining cable guide, wherein said insulating receiving element connected to the conductor frame, said adjoining cable guide, and said electrodes, are arranged symmetrically in relation to the axis of symmetry.

2. The measuring probe of claim 1, wherein the electrodes are comprised of noble metal.

3. The measuring probe of claim 1, wherein the individual conductors of the frame have been sand-blasted.

4. The measuring probe of claim 1, wherein the individual conductors of the frame are provided with notches at regular intervals.

5. The measuring probe of claim 1, wherein the thermoplastic is an ethylene/tetrafluoroethylene copolymer.

* * * * *